US00PP23911P3

(12) United States Plant Patent
Danziger

(10) Patent No.: US PP23,911 P3
(45) Date of Patent: Sep. 17, 2013

(54) ***EUPHORBIA* PLANT NAMED 'DIWAL2'**

(50) Latin Name: *Euphorbia hypercifolia*
Varietal Denomination: DIWAL2

(75) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 192 days.

(21) Appl. No.: 13/134,412

(22) Filed: Jun. 6, 2011

(65) Prior Publication Data

US 2012/0311751 P1 Dec. 6, 2012

(51) Int. Cl.
*A01H 5/00* (2006.01)

(52) U.S. Cl.
USPC ..... Plt./302

(58) Field of Classification Search
USPC ..... Plt./302
See application file for complete search history.

*Primary Examiner* — Kent L Bell
(74) *Attorney, Agent, or Firm* — Cassandra Bright

(57) ABSTRACT

A new and distinct *Euphorbia* cultivar named 'DIWAL2' is disclosed, characterized by a mass of foliage, early flowering and upright plant habit. The new variety forms a short plant with strong branching. The new variety is a *Euphorbia*, normally produced as an outdoor garden or container plant, with potential indoor use as well.

2 Drawing Sheets

Latin name of the genus and species: *Euphorbia hypercifolia.*

Variety denomination: 'DIWAL2'.

BACKGROUND OF THE INVENTION

The new *Euphorbia* cultivar is a product of a planned breeding program conducted by the inventor, Gavriel Danziger, in Moshav Mishmar Hashiva, Israel. The objective of the breeding program was to produce new *Euphorbia* varieties for ornamental commercial applications. The cross resulting in this new variety was made during October 2007.

The seed parent is the unpatented, proprietary seedling variety referred to as *Euphorbia hypercifolia* 'CV.8-1'. The pollen parent is unknown, as the crossing resulting in 'DIWAL2' was an open pollination, with an unidentifiable pollen parent. The new variety was discovered in April 2008 by the inventor in a group of seedlings resulting from the 2007, open pollination in a research greenhouse in Moshav Mishmar Hashiva, Israel.

Asexual reproduction of the new cultivar 'DIWAL2' by vegetative cuttings was first performed at a research greenhouse in Moshav Mishmar Hashiva, Israel in June 2008 and has shown that the unique features of this cultivar are stable and reproduced true to type in successive generations.

SUMMARY OF THE INVENTION

The cultivar 'DIWAL2' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DIWAL2'. These characteristics in combination distinguish 'DIWAL2' as a new and distinct *Euphorbia* cultivar:

1. Mass of foliage
2. Upright plant habit

3. Early flowering
4. Short plant habit
5. Strong branching.

Plants of the new cultivar 'DIWAL2' are similar to plants of the seed parent, *Euphorbia hypercifolia* 'CV.8-1' in most horticultural characteristics, however, plants of the new cultivar 'DIWAL2' have a more compact plant habit, and more bracts per plant. Additionally, the new cultivar begins flowering earlier and produces more lateral branches, producing a denser plant than the seed parent.

COMMERCIAL COMPARISON

Plants of the new cultivar 'DIWAL2' are comparable to the commercial variety *Euphorbia graminea* 'Inneuphdia' U.S. Plant Pat. No. 17,567. These *Euphorbia* varieties are similar in most horticultural characteristics, however, plants of the new variety 'DIWAL2' differ in having thinner bracts, earlier blooming and brighter foliage than 'Inneuphdia'. Additionally, the new variety forms denser plants with a mass foliage foliage not found with plants of 'Inneudphdia'.

BRIEF DESCRIPTION OF THE PHOTOGRAPHS

Figure 1:
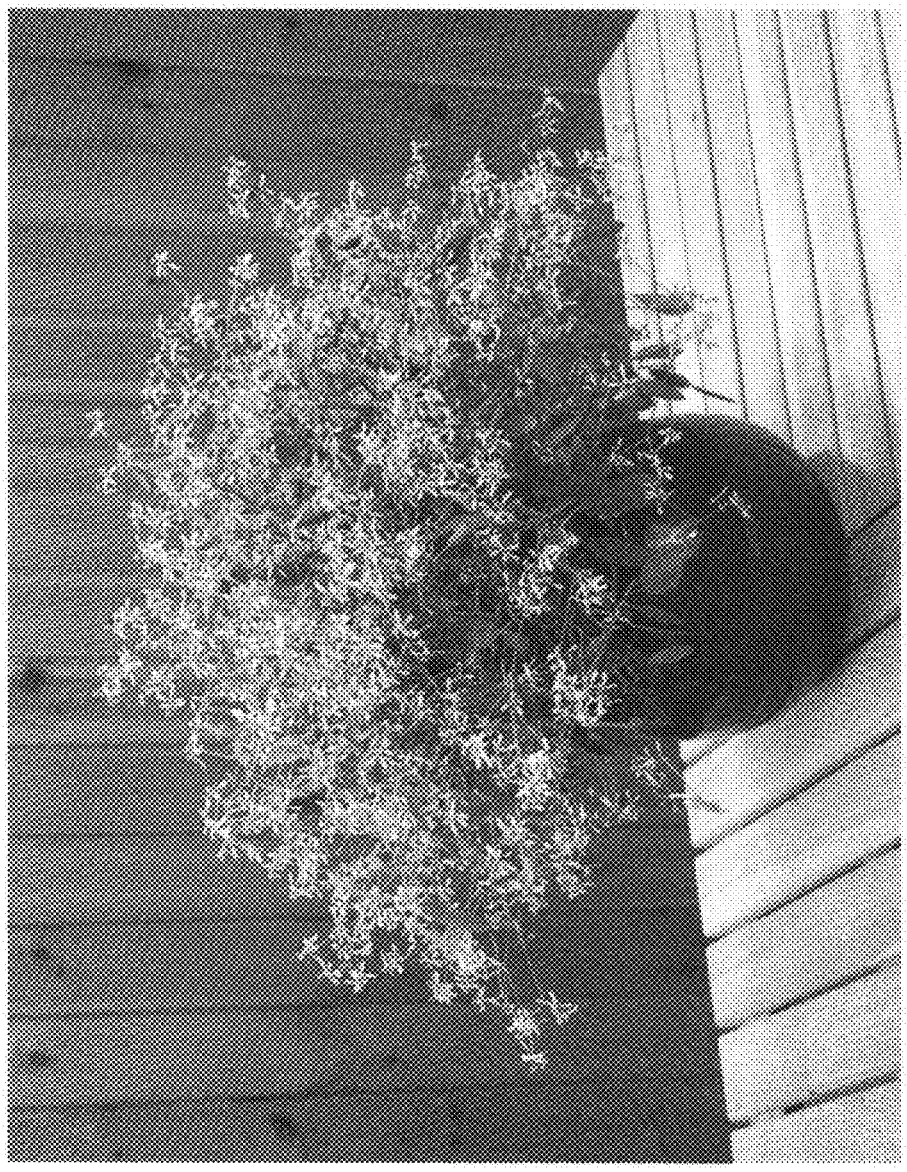

The accompanying photograph in FIG. 1 illustrates in full color a typical plant of 'DIWAL2' grown in a greenhouse, in a 13 cm basket. Age of the plant photographed is approximately 3 months from a rooted cutting.

Figure 2:
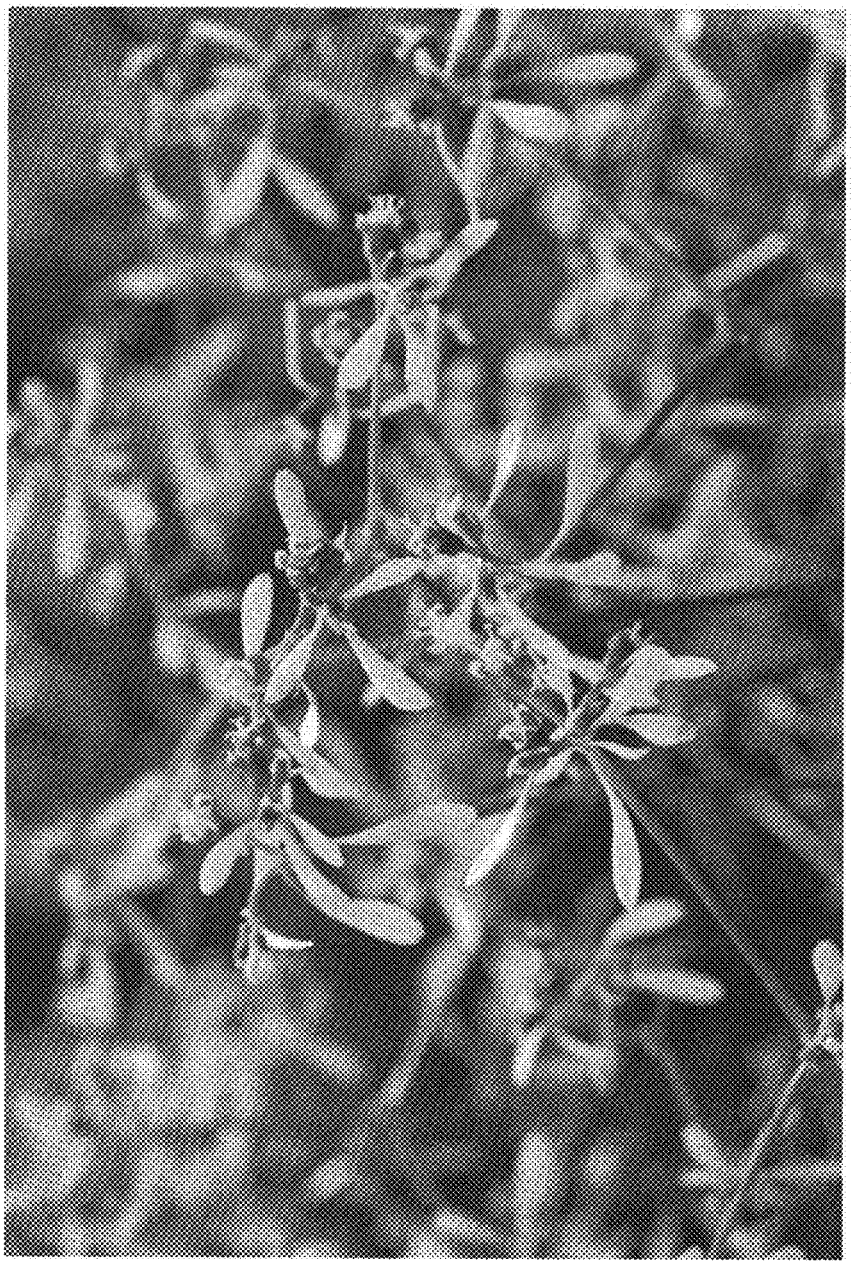

FIG. 2 illustrates in full color a close up of a typical bloom of 'DIWAL2'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2005 except where general terms of ordinary dictionary significance are used. The following observations and measurements describe 'DIWAL2' plants grown in a greenhouse during Spring in Moshav Mishmar Hashiva, Israel. The growing temperature ranged from 18° C. to 25° C. during the day and from 15° C. to 18° C. during the night. General light conditions are bright, normal sunlight. Measurements and numerical values represent averages of typical plant types.

Botanical classification: *Euphorbia hypercifolia* 'DIWAL2'.

PROPAGATION

Time to rooting: 15-19 days at approximately 20° C.

Root description: Fibrous, fleshy, medium thickness, white in color.

PLANT

Growth habit: Plant habit is compact and mounded. Plants upright to outwardly spreading; creating an inverted triangle shape.

Height: Approximately 25 cm.

Plant spread: Approximately 43 cm.

Growth rate: Moderate.

Branching characteristics: Freely branching, usually about 4 primary branches each with numerous secondary and tertiary lateral branches.

Length of lateral branches: Approximately 16 cm.

Diameter of lateral branches: Approximately 0.4 cm.

Texture of lateral branches: Smooth, glabrous.

Internode length: Approximately 4 cm.

Strength of stem: Strong.

Color of lateral branches: Near RHS Yellow-Green144A.

Angle of branches: 45°.

Number of leaves per lateral branch: Approximately 8 leaves.

FOLIAGE

Basal leaves:

*Arrangement*.—Opposite; Simple.

*Average length*.—Approximately 3.3 cm.

*Average width*.—Approximately 1.3 cm.

*Shape of blade*.—Elliptical.

*Apex*.—Acute.

*Base*.—Attenuate to acute.

*Attachment*.—Petiolate.

*Margin*.—Entire.

*Texture of top surface*.—Pubescent.

*Texture of bottom surface*.—Pubescent.

*Leaf internode length*.—Approximately 1.5 cm.

*Color*.—Young foliage upper side: Near RHS Green 137B. Young foliage under side: Near RHS Green 137C. Mature foliage upper side: Near RHS Green 137B. Mature foliage under side: Near RHS Green 137C.

*Venation*.—Type: Pinnate, arcuate. Venation color upper side: Near RHS Green 137A. Venation color under side: Near RHS Green 137C.

Petiole:

*Length*.—2 cm. Diameter: less than 1 mm.

*Color*.—Near RHS Yellow-Green 144B.

Whorl leaves:

*Arrangement*.—Opposite.

*Average length*.—Approximately 3 cm.

*Average width*.—Approximately 1.4 cm.

*Shape of blade*.—Elliptical.

*Apex*.—Acute.

*Base*.—Attenuate to acute.

*Attachment*.—Sessile.

*Margin*.—Entire.

*Texture of top surface*.—Pubescent.

*Texture of bottom surface*.—Pubescent.

*Color*.—Young foliage upper side: Near RHS Green 137A. Young foliage under side: Near RHS Green 137C. Mature foliage upper side: Near RHS Green 137A. Mature foliage under side: Near RHS Green 137C.

*Venation*.—

*Type*.—Pinnate, arcuate. Venation color upper side: Near RHS Green 137A. Venation color under side: Near RHS Green 137C.

FLOWER

Bloom period:

*Natural flowering season*.—Spring to summer in moderate climates flowering continuous during this period.

Bud:

*Bud shape*.—Flanged.

*Bud length*.—Approximately 4 mm.

*Bud diameter*.—Approximately 1.7 mm.

*Bud color*.—Near RHS Green 143B.

Inflorescence:

*Form*.—Single rotate flowers arranged in umbel-like compound terminal cymes. Freely flowering with numerous flower buds and flowers per plant. Flower face upright and outwardly.

*Cyme depth*.—2.2 cm.

*Cyme diameter*.—5 cm.

*Diameter of entire inflorescence*.—Approximately 2 cm.

*Depth of entire inflorescence*.—Approximately 1.2 cm.

Individual flowers:

*Length*.—Approximately 5 mm.

*Width*.—Approximately 3 mm.

*Aspect*.—Horizontal.

*Duration on plant*.—About 10 days.

*Persistent or self-cleaning flowers*.—Persistent.

Fragrance: Not detected.

Floral bracts:

*Arrangement*.—Opposite or whorled.

*Quantity*.—1 to 3, most commonly 3.

*Shape*.—Ovate to lanceolate.

*Apex*.—Obtuse.

*Base*.—Acute.

*Margin*.—Entire.

*Length*.—About 10 mm.

*Width*.—About 3 mm.

*Texture*.—Smooth.

*Color*.—Upper side of immature bract: RHS White N999D. Under side of immature bract: RHS White N999D. Upper side of mature bract: RHS White N999D. Under side of mature bract: RHS White N999D.

Bract petiole:

*Length*.—Average 0.7 cm.

*Width*.—About 0.15 mm.

*Texture*.—Smooth.

*Color*.—Near RHS Yellow-Green 144C.

Cyathia:

*Arrangement*.—Upright.

*Single cyathia*.—Height: Approx. 6 mm. Diameter: Approx 3 mm. Color Immature: Near RHS Yellow-Green 145A. Color Mature: Near RHS Yellow-Green 145A.

*Cyathia cluster*.—Height: Average 11 cm (highly variable). Diameter: Average 14 cm (highly variable). Cyathia per corymb: Between 18 and 60 (highly variable).

Peduncle:

*Peduncle length*.—Approximately 4 cm to 5 cm.

*Peduncle diameter*.—Approximately 1 mm.

*Angle*.—Approximately 60-90 deg from center of whorl.

*Color*.—Near RHS Green 143A.

*Peduncle texture*.—Smooth, glabrous.

Pedicels:

*Length*.—Approx. 3 mm.

*Diameter*.—Approx. 0.5 mm.

*Angle*.—About 45 deg from vertical.

*Strength*.—Strong.

*Texture*.—Glabrous, smooth.

*Color*.—Near RHS Yellow-Green 144A.

REPRODUCTIVE ORGANS

Androecium:

*Stamens*.—About 4 stamens per cyathia. Anther shape: Oval, bi-lobed. Anther length: Less then 1 mm. Anther color: Near RHS Orange-White 159B. Pollen quantity: Moderate. Pollen color: Near RHS White 155A.

Gynoecium: Pistil number: 1. Pistil shape: rounded ovary with a crested stigma. Pistil length: Approx. 3 mm. Style length: Less then 1 mm. Style color: Near RHS White N999D. Stigma shape: Crested. Stigma color: Near RHS White N999D. Ovary diameter: Less then 1 mm. Ovary color: Near RHS Yellow-Green 144A.

OTHER CHARACTERISTICS

Fruit/seed production:

*Shape*.—3-lobed capsule, usually containing 3 seeds.

*Color*.—Near RHS Green137D.

*Size*.—About 3 mm for a mature fruit.

Disease resistance: Good resistance to normal diseases of *Euphorbia hypercifolia*.

Temperature tolerance: Tolerates a temperature range between 10° C. to 40° C.

What is claimed is:

1. A new and distinct cultivar of *Euphorbia* plant named 'DIWAL2' as herein illustrated and described.

* * * * *